US00PP29633P3

(12) United States Plant Patent
Olesen

(10) Patent No.: US PP29,633 P3
(45) Date of Patent: Sep. 4, 2018

(54) MINIATURE ROSE PLANT NAMED 'POULPAH085'

(50) Latin Name: ***Rosa* hybrid**
Varietal Denomination: Poulpah085

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 71 days.

(21) Appl. No.: 15/330,290

(22) Filed: Sep. 6, 2016

(65) Prior Publication Data

US 2018/0070494 P1 Mar. 8, 2018

(51) Int. Cl.
*A01H 5/02* (2018.01)

(52) U.S. Cl.
USPC ..... Plt./117
CPC ..... *A01H 5/0222* (2013.01)

(58) Field of Classification Search
USPC ..... Plt./117
See application file for complete search history.

*Primary Examiner* — Keith O Robinson

(57) ABSTRACT

A new garden rose plant of the Miniature class which has abundant, near white flowers and attractive foliage. This new and distinct variety has shown to be uniform and stable in the resulting generations from asexual propagation.

1 Drawing Sheet

Botanical designation: *Rosa* hybrid.
Variety denomination: 'Poulpah085'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpah085', originated as a single seedling from the stated cross.

The new variety may be distinguished from its male pollen parent and female seed parent primarily by the following characteristics. The male pollen parent plant has light yellow flowers, while the new variety has near white flowers. The female seed parent plant is more compact in growth height, reaching 25 cm in one season, while the new variety grows to 35 cm in one season.

The objective of the hybridization of this rose variety was to create a new and distinct variety for garden use with unique qualities, such as:

1. Uniform and abundant near white flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah085' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpah085' was selected in the spring of 2011 by the inventor as a single plant from the progeny of the aforementioned hybridization.

Asexual reproduction of 'Poulpah085' by traditional budding and rooted cuttings was first done by Mogens N. Olesen in the nursery in Fredensborg, Denmark in July, 2011. This initial and other subsequent asexual propagations conducted in controlled environments have demonstrated that the characteristics of 'Poulpah085' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah085'. Specifically illustrated in the drawing are an open flower, flower in parts with petals detached, sepals detached, bare stems, leaves, and a cluster of flowers on a branch. Plants shown are 2 years of age.

DETAILED DESCRIPTION OF THE VARIETY

The following is a description of 'Poulpah085', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah051', U.S. Plant Pat. No. 24,222 are compared to 'Poulpah085' in Chart 1.

CHART 1

| | 'Poulpah085' | 'Poulpah051' |
|---|---|---|
| Petal Count | 45 | 50 |
| Flower Diameter | 70 mm | 35 to 40 mm |

CHART 1-continued

| | 'Poulpah085' | 'Poulpah051' |
|---|---|---|
| General Tonality of Flower Color | White Group 155B | White Group 155A |

FLOWER AND FLOWER BUD

Blooming habit: Continuous.

Flower bud:

*Size*.—Upon opening, 16 mm in length from base of receptacle to end of bud. Bud diameter is 14 mm.

*Bud form*.—Ovoid.

*Bud color*.—As sepals divide petals are Yellow Group 8D with streaks of Red Group 36A.

*Sepal inner surface*.—Color: Yellow-Green Group 147D. Surface: Lightly pubescent.

*Sepal outer surface*.—Color: Yellow-Green Group 144A with intonations of Greyed-Red Group 178B. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—21 mm long, 11 mm wide.

*Receptacle*.—Texture: Smooth. Size: 5 mm in height, 6 mm wide. Color: Yellow-Green Group 144A. Shape: Campanulate.

*Pedicel*.—Surface: Smooth. Length: About 30 mm. Diameter: 3 mm on average. Color: Yellow-Green Group 144A. Strength: Strong.

*Peduncle*.—Length: 2 to 3 cm. Diameter: About 3 mm. Color: Yellow-Green Group 145A. Texture: Smooth.

Flower bud development: Flower buds are borne in clusters of 3 to 5 flower buds per stem.

Flower bloom:

*Fragrance*.—Strong perfume.

*Duration*.—The blooms have a duration on the plant of approximately 10 days. Petals fall cleanly away from plant after flowers have fully matured.

*Size*.—Flower diameter is 70 mm when open. Flower depth is 25 mm.

*Flower shape*.—Rosette, double, with many slightly overlapping petals of different sizes.

Petalage: Under normal conditions, flowers have 45 petals total.

General tonality of flower: Open flowers are White Group 155B.

Petal color:

*Upon opening, outer petals*.—Upper surface: White Group 155B. Lower surface: White Group 155B with occasional streaks of Red Group 50 B.

*Upon opening, inner petals*.—Upper surface: White Group 155B. Lower surface: White Group 155B.

*Basal petal spots, upon opening*.—Yellow Group 4D on upper and lower surface.

Petals:

*Petal reflex*.—Slightly reflexed.

*Margin*.—Entire and uniform. Moderate undulations.

*Shape*.—Broad and rounded. Apex shape: Rounded. Base shape: Rounded.

*Size*.—35 mm (l)×40 mm (w).

*Texture*.—Smooth.

*Thickness*.—Average.

Petaloids:

*Size*.—18 mm (l) by 10 mm (w).

*Quantity*.—About 6.

*Shape*.—Apex is rounded, base is acute.

*Color*.—White Group 155B.

Reproductive flower parts:

*Pollen*.—None observed.

*Anthers*.—Size: 2 mm in length. Color: Greyed-Yellow Group Quantity: 35 on average.

*Filaments*.—Color: Green-White Group 157A. Length: 5 mm.

*Pistils*.—Length: 3 mm. Quantity: 20 on average.

*Stigmas*.—Color: Yellow-Green Group 145D.

*Styles*.—Color: Yellow-Green Group 145D.

*Location of stigmas*.—Level in location relative to the length of the filaments and the height of the anthers.

*Hips*.—None Observed.

PLANT

Plant growth: Upright, bushy. Plants are 35 cm in height, and 30 cm wide.

Stems:

*Color*.—Juvenile growth: Yellow-Green Group 144B. Mature growth: Yellow-Green Group 144A.

*Length*.—On average, canes are 20 cm from the base of the plant to the flowering portion.

*Diameter*.—6 mm.

*Internodes*.—On mature canes about 27 mm between nodes.

*Surface texture*.—Young wood: Smooth. Older wood: Smooth.

Long prickles:

*Incidence*.—15 prickles per 10 cm of stem.

*Size*.—Average length of prickles on mature stems is 7 mm.

*Shape*.—Upper portion is linear. Lower portion is concave.

*Color*.—Juvenile prickles: Yellow-Green Group 152D. Mature prickles: Greyed-Yellow Group 160A with intonations of Greyed-Orange Group 176C.

Plant foliage:

*Compound leaf*.—100 mm (l)×70 (w).

*Quantity*.—3 leaves per 10 cm of stem on average.

*Leaf bearing angle to the stem*.—45 degrees.

*Color of juvenile foliage*.—Upper side: Yellow-Green Group 144A with Greyed-Purple Group at margins. Lower side: Yellow-Green Group 144B with Greyed-Purple Group at margins.

*Color of mature foliage*.—Upper side: Yellow-Green Group 147A. Lower side: Yellow-Green Group 146B.

Plant leaves and leaflets:

*Stipules*.—Size: 5 mm long, 2 mm wide. Quantity: 2 per compound leaf. Shape: Linear, slightly broad based with outward extending apices. Margins: Finely serrated. Color:.

*Petiole*.—Length: 22 mm. Diameter: 2 mm.

*Upper surface*.—Color: Yellow-Green Group 144A.

*Lower surface*.—Color: Yellow-Green Group 144A.

*Rachis*.—Length: 30 mm.

*Upper surface*.—Color: Yellow-Green Group 144A.

*Lower surface*.—Color: Yellow-Green Group 144A.

*Leaflet*.—Quantity: Normally 5 to 7 leaflets. Margins: Serrated. Size: On average terminal leaflets are 45 mm long, 28 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah085', substantially as illustrated and described herein, due to its abundant near white flowers, disease resistance, and extended period of bloom.

* * * * *

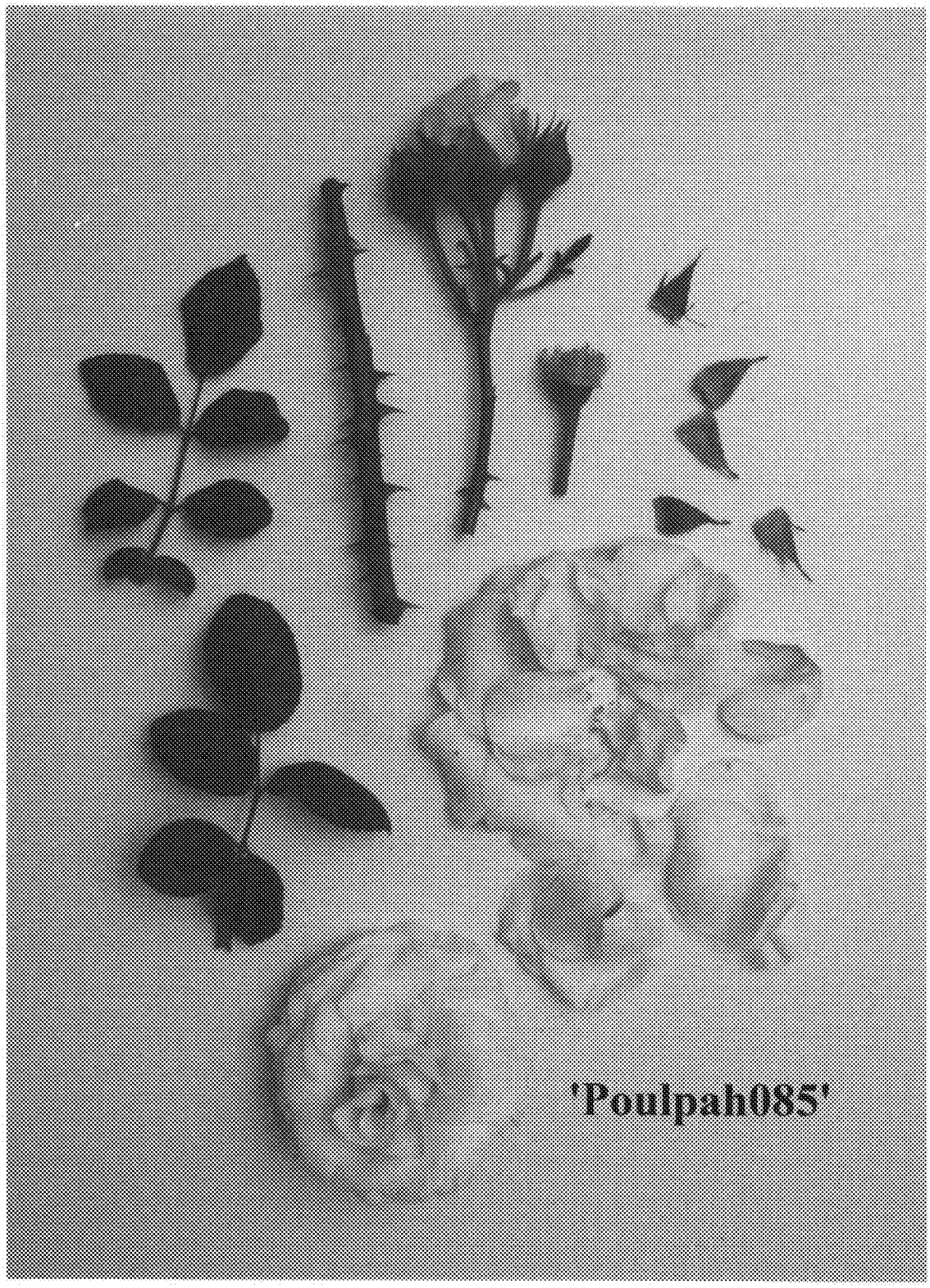
'Poulpah085'